US008523043B2

(12) United States Patent
 Ullrich et al.

(10) Patent No.: US 8,523,043 B2
(45) Date of Patent: Sep. 3, 2013

(54) SURGICAL STAPLER HAVING HAPTIC FEEDBACK

(75) Inventors: Christopher Ullrich, Ventura, CA (US);
 Ali Modarres, Mont-Royal (CA); Pedro Gregorio, Vardun (CA); Cheryl Shimek, Oakland, CA (US)

(73) Assignee: Immersion Corporation, San Jose, CA (US)

(*) Notice: Subject to any disclaimer, the term of this patent is extended or adjusted under 35 U.S.C. 154(b) by 323 days.

(21) Appl. No.: 12/962,467

(22) Filed: Dec. 7, 2010

(65) Prior Publication Data

US 2012/0138658 A1 Jun. 7, 2012

(51) Int. Cl.
 *A61B 17/068* (2006.01)

(52) U.S. Cl.
 USPC ............ 227/180.1; 227/19; 227/175.1

(58) Field of Classification Search
 USPC .............. 128/898; 227/19, 175.1, 180.1
 See application file for complete search history.

(56) References Cited

U.S. PATENT DOCUMENTS

| | | |
|---|---|---|
| 3,785,381 A | 1/1974 | Lower et al. |
| 4,841,987 A | 6/1989 | Brown et al. |
| 5,047,046 A | 9/1991 | Bodoia |
| 5,188,111 A | 2/1993 | Yates et al. |
| 5,339,799 A | 8/1994 | Kami et al. |
| 5,357,956 A | 10/1994 | Nardella |
| 5,389,849 A | 2/1995 | Asano et al. |
| 5,411,511 A | 5/1995 | Hall |
| 5,503,320 A | 4/1996 | Webster et al. |
| 5,529,235 A * | 6/1996 | Boiarski et al. ............ 227/175.1 |
| 5,609,607 A | 3/1997 | Hechtenberg et al. |
| 5,623,582 A | 4/1997 | Rosenberg |
| 5,649,934 A | 7/1997 | Smeltzer, III et al. |
| 5,685,474 A | 11/1997 | Seeber |
| 5,713,896 A * | 2/1998 | Nardella ........................ 606/50 |
| 5,728,044 A | 3/1998 | Shan |
| 5,733,281 A | 3/1998 | Nardella |

(Continued)

FOREIGN PATENT DOCUMENTS

| | | |
|---|---|---|
| CA | 2520942 | 3/2007 |
| DE | 4213426 | 10/1992 |

(Continued)

OTHER PUBLICATIONS

EP Appl. No. 11 17 6993, Extended European Search Report, dated Nov. 8, 2011.

(Continued)

*Primary Examiner* — Brian D Nash
(74) *Attorney, Agent, or Firm* — Medler Ferro PLLC (57) ABSTRACT

A surgical tool system includes a surgical tool for cutting and stapling tissue and a tactile feedback system integrated onto a handle of the tool that generates relevant feedback in at least the form of haptic effects to the user. The tactile feedback alerts the user of tissue properties, i.e., the type of tissue or other structures located within the jaws of the stapler, whether the quantity or thickness of tissue located within the jaws of the stapler is appropriate for the selected stapler cartridge, whether the proper length of staples has been fired based on the length of tissue located in the jaws, whether a blood vessel is located within the jaws of the stapler, whether the stapling process has successfully sealed the tissue located within the jaws of the stapler, the position of the cutting element, and/or when the stapling procedure or firing cycle is completed.

20 Claims, 9 Drawing Sheets

(56) References Cited

U.S. PATENT DOCUMENTS

| | | | |
|---|---|---|---|
| 5,771,902 A | 6/1998 | Lee et al. | |
| 5,810,880 A | 9/1998 | Jensen et al. | |
| 5,833,634 A | 11/1998 | Laird et al. | |
| 5,836,894 A | 11/1998 | Sarvazyan | |
| 5,928,158 A | 7/1999 | Aristides | |
| 5,928,159 A | 7/1999 | Eggers et al. | |
| 5,950,629 A | 9/1999 | Taylor et al. | |
| 5,965,880 A | 10/1999 | Wolf et al. | |
| 5,989,199 A | 11/1999 | Cundari et al. | |
| 6,004,335 A * | 12/1999 | Vaitekunas et al. | 606/169 |
| 6,024,741 A * | 2/2000 | Williamson et al. | 606/40 |
| 6,063,031 A | 5/2000 | Cundari et al. | |
| 6,096,004 A | 8/2000 | Meglan et al. | |
| 6,132,441 A | 10/2000 | Grace | |
| 6,190,334 B1 | 2/2001 | Lasky et al. | |
| 6,375,471 B1 | 4/2002 | Wendlandt et al. | |
| 6,423,057 B1 | 7/2002 | He et al. | |
| 6,436,107 B1 | 8/2002 | Wang et al. | |
| 6,494,882 B1 | 12/2002 | Lebouitz et al. | |
| 6,594,552 B1 | 7/2003 | Gerbi et al. | |
| 6,690,963 B2 | 2/2004 | Ben-Haim et al. | |
| 6,718,196 B1 | 4/2004 | Mah et al. | |
| 6,730,021 B2 | 5/2004 | Vassiliades, Jr. et al. | |
| 6,810,281 B2 | 10/2004 | Brock et al. | |
| 6,817,973 B2 | 11/2004 | Merril et al. | |
| 6,969,384 B2 | 11/2005 | de Juan, Jr. et al. | |
| 7,108,695 B2 | 9/2006 | Witt et al. | |
| 7,118,582 B1 | 10/2006 | Wang et al. | |
| 7,122,028 B2 | 10/2006 | Looper et al. | |
| 7,206,627 B2 | 4/2007 | Abovitz et al. | |
| 7,280,863 B2 | 10/2007 | Shachar | |
| 7,300,450 B2 | 11/2007 | Vleugels et al. | |
| 7,366,562 B2 | 4/2008 | Dukesherer et al. | |
| 7,373,219 B2 | 5/2008 | Nowlin et al. | |
| 7,422,139 B2 | 9/2008 | Shelton, IV et al. | |
| 7,720,532 B2 | 5/2010 | Hashimshony et al. | |
| 7,771,424 B2 | 8/2010 | McGaffigan | |
| 7,963,192 B2 | 6/2011 | Mayenberger et al. | |
| 8,216,212 B2 | 7/2012 | Grant et al. | |
| 2001/0004700 A1 | 6/2001 | Honeycutt et al. | |
| 2001/0025150 A1 | 9/2001 | de Juan, Jr. et al. | |
| 2002/0112547 A1 | 8/2002 | Eltaib et al. | |
| 2002/0120188 A1 | 8/2002 | Brock et al. | |
| 2003/0023250 A1 | 1/2003 | Watschke et al. | |
| 2003/0057973 A1 | 3/2003 | Nojima et al. | |
| 2004/0009459 A1 | 1/2004 | Anderson et al. | |
| 2004/0019447 A1 | 1/2004 | Shachar | |
| 2004/0106916 A1 | 6/2004 | Quaid et al. | |
| 2004/0167559 A1 | 8/2004 | Taylor et al. | |
| 2005/0021024 A1 | 1/2005 | Hooven | |
| 2005/0090815 A1 | 4/2005 | Francischelli et al. | |
| 2005/0131390 A1 * | 6/2005 | Heinrich et al. | 606/1 |
| 2005/0223327 A1 | 10/2005 | Cunningham et al. | |
| 2005/0245910 A1 | 11/2005 | Wright et al. | |
| 2006/0033703 A1 | 2/2006 | Olien et al. | |
| 2006/0095033 A1 | 5/2006 | Garabedian et al. | |
| 2006/0142657 A1 | 6/2006 | Quaid et al. | |
| 2006/0207978 A1 | 9/2006 | Rizun et al. | |
| 2006/0278680 A1 * | 12/2006 | Viola et al. | 227/176.1 |
| 2006/0279534 A1 | 12/2006 | Powers et al. | |
| 2006/0293643 A1 | 12/2006 | Wallace et al. | |
| 2007/0062147 A1 | 3/2007 | Pappone | |
| 2007/0073282 A1 | 3/2007 | McGaffigan et al. | |
| 2007/0112284 A1 | 5/2007 | Hoffman et al. | |
| 2007/0135735 A1 | 6/2007 | Ellis et al. | |
| 2007/0142749 A1 | 6/2007 | Khatib et al. | |
| 2007/0175962 A1 | 8/2007 | Shelton, IV et al. | |
| 2007/0175964 A1 * | 8/2007 | Shelton et al. | 227/180.1 |
| 2007/0270884 A1 * | 11/2007 | Smith et al. | 606/139 |
| 2007/0279401 A1 | 12/2007 | Ramstein et al. | |
| 2008/0009747 A1 | 1/2008 | Saadat et al. | |
| 2008/0086120 A1 | 4/2008 | Mirza et al. | |
| 2008/0117166 A1 | 5/2008 | Rosenberg | |
| 2008/0167662 A1 | 7/2008 | Kurtz | |
| 2008/0167672 A1 * | 7/2008 | Giordano et al. | 606/167 |
| 2008/0197167 A1 * | 8/2008 | Viola et al. | 227/176.1 |
| 2008/0251569 A1 * | 10/2008 | Smith et al. | 227/175.1 |
| 2009/0090763 A1 * | 4/2009 | Zemlok et al. | 227/175.2 |
| 2009/0163904 A1 | 6/2009 | Miller et al. | |
| 2010/0179423 A1 | 7/2010 | Ramstein et al. | |
| 2011/0046659 A1 | 2/2011 | Ramstein et al. | |
| 2011/0062211 A1 | 3/2011 | Ross et al. | |
| 2011/0288573 A1 * | 11/2011 | Yates et al. | 606/170 |
| 2012/0041436 A1 | 2/2012 | Ullrich et al. | |
| 2012/0143182 A1 | 6/2012 | Ullrich | |

FOREIGN PATENT DOCUMENTS

| | | |
|---|---|---|
| EP | 1 254 637 | 11/2002 |
| EP | 2 044 890 | 4/2009 |
| EP | 2 218 409 | 8/2010 |
| EP | 2 277 458 | 1/2011 |
| EP | 2 283 781 | 2/2011 |
| EP | 2 417 925 | 2/2012 |
| WO | WO 94/24949 | 11/1994 |
| WO | WO 03/020139 | 3/2003 |
| WO | WO 03/090630 | 11/2003 |
| WO | WO 2004/067053 | 8/2004 |
| WO | WO 2005/013803 | 2/2005 |
| WO | WO 2005/110304 | 11/2005 |
| WO | WO 2008/033937 | 3/2008 |
| WO | WO-2009/009220 A2 | 1/2009 |
| WO | WO-2009/009220 A3 | 1/2009 |
| WO | WO-2010/008663 A1 | 1/2010 |
| WO | WO-2010/065314 A1 | 6/2010 |
| WO | WO-2010/083060 A1 | 7/2010 |

OTHER PUBLICATIONS

EP Appl. No. 11 19 1549, Extended European Search Report, dated Feb. 22, 2012.

"Tactile Sensor Acts as a Human Finger in Minimally Invasive Surgery", www.physorg.com/news102155952.html, 2007.

Bethea, et al., Abstract of: "Application of Haptic Feedback to Robotic Surgery", http://www.liebertonline.com/doi/abs/10.1089/1092642041255441, Downloaded: Nov. 25, 2008.

Bholat, et al., Abstract of: "Tactile Feedback is Present During Minimally Invasive Surgery", J Am Coil Surg, Oct. 1999, 189(4), pp. 349-55; http://www.ncbi.nlm.nih.gov/pubmed/10509459, Downloaded: Nov. 25, 2008.

Hannaford, et al., "Computerized Endoscopic Surgical Grasper", Proceedings, Medicine Meets Virtual Reality, San Diego, CA, Jan. 1998.

Hu, et al., "Real-Time Haptic Feedback in Laparoscopc Tools for Use in Gastro-Intestinal Surgery", T. Dohi and R. Kikinis (Eds.): MICCAI 2002, LNCS 2488, (2002), pp. 66-74.

Marvik, et al., Abstract of: "Ergonomic Design Criteria for a Novel Laparoscopic Tool Handle with Tactile Feedback", Minerva Chirurgica ISSN 0026-4733, vol. 61, No. 5, (2006), pp. 435-444.

Moy, et al., Abstract of: "A Compliant Tactile Display for Teletaction", http://ieeexplore.ieee.org/xpl/freeabs_all.jsp?tp=&arnumber=845247&isnumber=18324, Downloaded: Nov. 25, 2008.

Okamura, et al., "The Haptic Scissors: Cutting in Virtual Environments", Proceedings of the 2003 IEEE International Conference on Robotics & Automation, Taipei, Taiwan, Sep. 14-19, 2003.

Schirmbeck, et al., "Tactile Feedback without Direct Touch: An Achievement for Robotically Working Heart Surgeons?", nereja.free.fr/files/BMT2005Haptic1.pdf, Downloaded: Nov. 25, 2008.

Yao, et al., "A Tactile Enhancement Instrument for Minimally Invasive Surgery", Computer Aided Surgery, vol. 10, No. 4, pp. 233-239, MICCAI (2004), pp. 89-96.

International Search Report for PCT/US2012/047006, (Oct. 5, 2012).

* cited by examiner

SURGICAL STAPLER HAVING HAPTIC FEEDBACK

FIELD OF THE INVENTION

Embodiments hereof relate to surgical tools for treating tissue, wherein information related to the tissue treatment is processed and displayed to a user in one or more feedback modes integrated onto a handle of the tool.

BACKGROUND OF THE INVENTION

As opposed to open surgery in which a surgeon cuts a relatively large incision in the skin of a patient for accessing internal organs, minimally invasive surgical procedures are performed by making relatively small incisions and then inserting tools through the incisions to access the organs. Minimally invasive surgery usually results in shorter hospitalization times, reduced therapy requirements, less pain, less scarring, and fewer complications.

Although minimally invasive surgical procedures involving small incisions include many advantages over open surgery, minimally invasive surgery can still create challenges to a surgeon. For example, the surgeon must typically rely on a miniature camera introduced through an incision to view the patient's internal organs and see how the movement and operation of the tools affects the organs. The camera transmits images to a visual display, allowing the surgeon to see the internal organs and tissues and to see the effect of other minimally invasive tools on the organs and tissues. In this way, the surgeon is able to perform laparoscopic surgery, dissection, cauterization, endoscopy, telesurgery, and the like.

Compared to open surgery, however, minimally invasive surgery presents limitations in visual and haptic perceptions, and creates challenges unique to this type of surgery. One of the major concerns relevant to both open surgery and minimally invasive surgery is the potential for tissue damage, possibly caused by inappropriate use of force. For example, surgical staplers include a distal end that simultaneously make a longitudinal incision in tissue and applies lines of staples on opposing sides of the incision. The distal end of the surgical stapler includes jaws for clamping or gripping tissue and the user fires the surgical stapler with a single firing stroke, or multiple firing strokes, depending on the device. In both open surgery and minimally invasive surgery, the tissue being stapled is clamped within the jaws of the surgical stapler and is not visible to the user, and therefore direct visualization is not helpful in certain tissue properties relevant to the surgical procedure. Firing the surgical stapler causes severing and stapling of the clamped tissue. In motor-driven surgical staplers, the cutting/stapling operation is actuated by merely pressing a button or firing trigger. However, users prefer to maintain control of deploying the staple and have the ability to stop deployment at anytime if the forces felt in the handle of the device feel too great or for some other clinical reason. Accordingly, there is a need for improved surgical staplers and in particular, there is a need for motor-driven surgical staplers having improved feedback related to the surgical procedure.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" refer to a position distant from or in a direction away from the clinician. "Proximal" and "proximally" refer to a position near or in a direction toward the clinician.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Embodiments hereof relate to a surgical tool system 101 that includes a laparoscopic stapler 100 for cutting and stapling tissue, a control system 112 for processing sensor information from tool 100, and a tactile feedback system 120 integrated into tool 100 that generates relevant feedback in at least the form of haptic effects to the user. As will be explained in more detail herein, the tactile feedback provided by feedback system 120 alerts the tool user of tissue properties such as but not limited to the type of tissue or other structures located within the jaws of the stapler (i.e., tissue anisotropy), whether the thickness of tissue located within the jaws of the stapler is appropriate for the selected stapler cartridge, whether the length of tissue located within the jaws of the stapler is appropriate for the selected stapler cartridge, whether a blood vessel is located within the jaws of the stapler, the position of the cutting element, and/or when the stapling procedure or firing cycle is completed.

Figure 1:
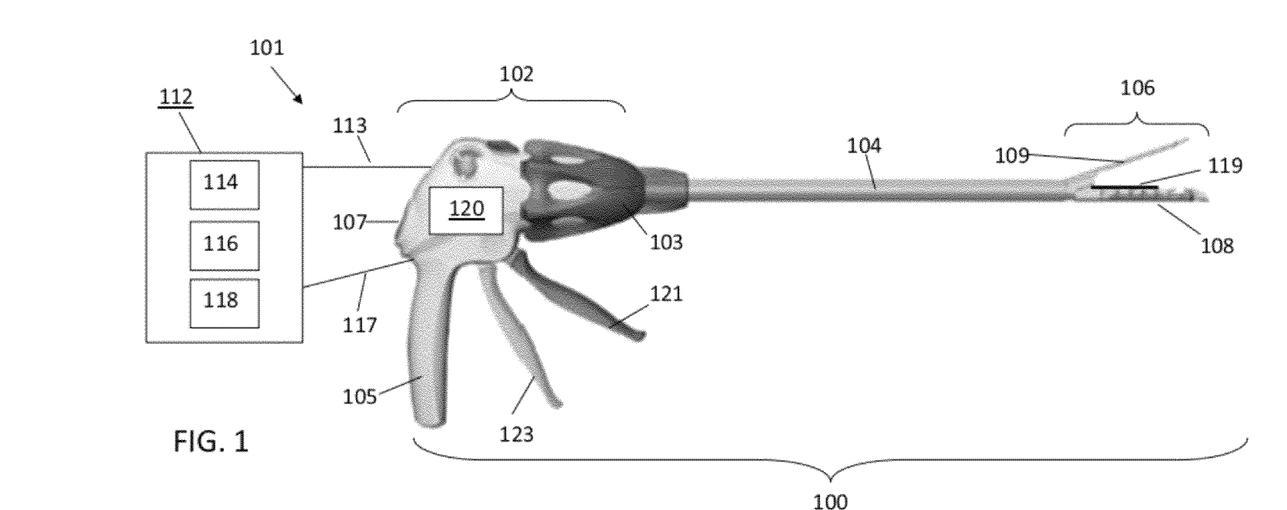
FIG. 1 is a diagram illustrating a side view of a surgical tool system including a laparoscopic surgical tool and an external control system according to an embodiment hereof.
Figure 2:
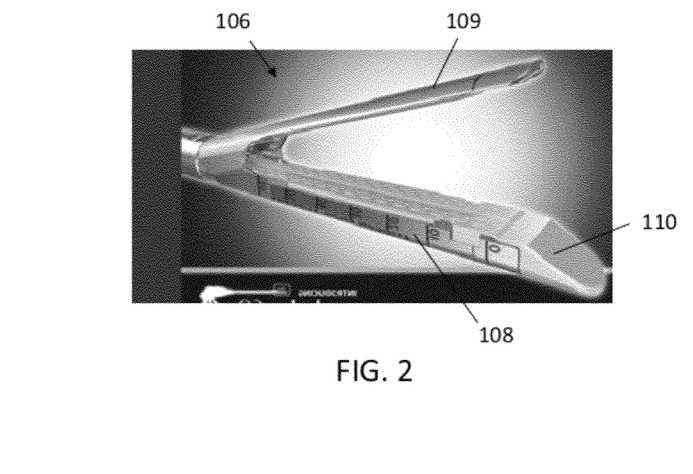
FIG. 2 is an enlarged perspective view of the distal end of FIG. 1.

FIGS. 1-5 illustrate an embodiment of an exemplary surgical tool system 101 that includes a surgical tool or stapler 100 and a control system 112. Referring to FIGS. 1 and 2, in one embodiment, stapler 100 is a laparoscopic tool which is configured to be inserted through a trocar or other minimally invasive access port. In another embodiment (not shown), stapler 100 is a surgical tool adapted for an open medical tissue-sealing procedure. Stapler 100 includes a handle portion 102, a shaft 104, and a distal portion 106 having jaw members 108, 109 for clamping and stapling tissue therebetween as will be explained in more detail herein. As best shown in FIG. 2, jaw member 108 forms an elongated channel sized to releasably receive a staple cartridge 110 having at least two laterally spaced rows of staples therein (not shown), and jaw member 109 defines a pivotally translatable clamping member or anvil having staple-forming pockets (not shown) aligned with the rows of staples in the cartridge. Tool 100 also includes a cutting element 119 that may be longitudinally advanced within jaw members 108, 109 for cutting or transecting clamped tissue. For illustrative purposes only, cutting element 119 is shown in FIG. 1 as partially deployed within open jaw members 108, 109. As will be understood by those of ordinary skill in the art, in operation cutting element 119 is only advanced/deployed when jaw members 108, 109 are closed together with tissue clamped therein. Shaft 104 is designed to connect handle portion 102 to distal portion 106 and to communicate mechanical actions of handle portion 102 to distal portion 106. For example, operation of handle portion 102 opens and closes jaw members 108, 109 through an internal mechanical connector (not shown) that runs from handle portion 102 to distal portion 106. According to some examples of the embodiment of FIG. 1 in which stapler 100 is a laparoscopic tool, shaft 104 may be about 20 cm to 30 cm in length and distal portion 106 may be between 6 and 8 cm in length. In addition the shaft 104 is typically 10 or 12 mm in diameter, although tools with 3 mm and 5 mm diameters are also sometimes used.

Figure 3:
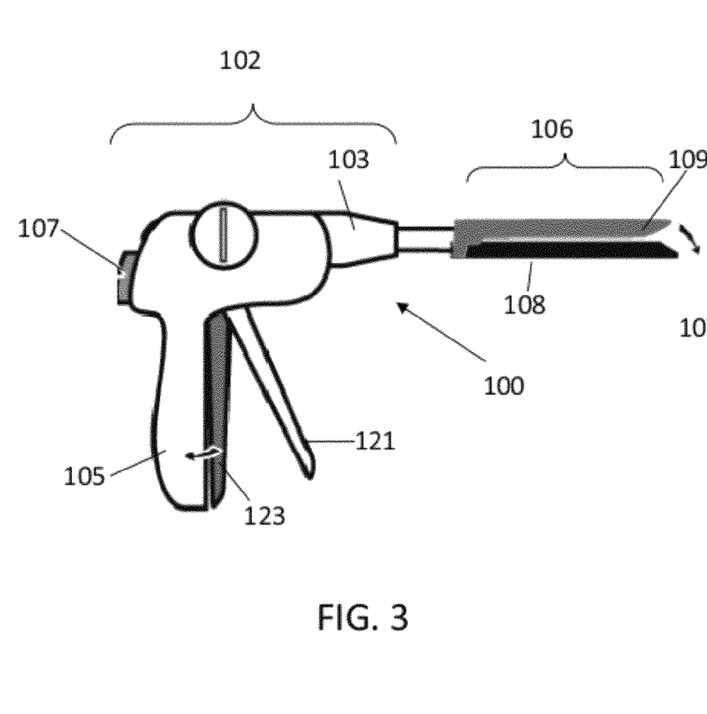
FIGS. 3 and 4 are diagrams illustrating operation of the surgical tool of FIG. 1, with FIG. 3 illustrating how to clamp tissue within the distal end of the surgical tool and FIG. 4 illustrating how to fire staples into the clamped tissue.
Figure 4:
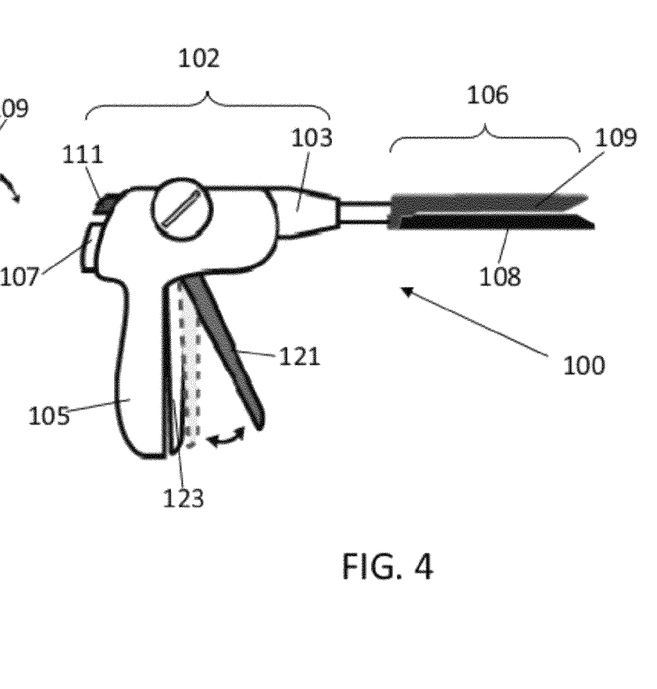

Handle portion 102 includes a handle grip 105, a closure trigger 123, and a firing trigger 121. In an embodiment, handle portion 102 may also include a rotatable knob 103 for rotating jaw members 108, 109 into position to grasp and clamp tissue. In operation, closure trigger 121 is actuated first. After tissue is positioned between the jaw members, jaw members 108, 109 are closed together to clamp tissue therebetween. By drawing closure trigger 121 back into a position directly adjacent to handle grip 105 as shown in FIG. 3, jaw member or anvil 109 closes towards jaw member 108 to clamp tissue positioned between the anvil and staple cartridge 110 located within jaw member 108. A locking pin (not shown) may be located on staple cartridge 110 to be engaged by the anvil when the anvil is closed into the tissue-clamping position. After tissue clamping has occurred, firing trigger 121 may then be actuated by moving firing trigger 121 toward handle grip 105 as shown in FIG. 4 to cause cutting and stapling of the clamped tissue. In one embodiment using a mechanical stapler (i.e. non motor-driven stapler), actuation of firing trigger 121 causes a manual release firing button 111 to pop out, which may be utilized by the user at any time during the procedure to manually stop staple deployment for any clinical reason. More particularly, tool 100 simultaneously makes a longitudinal incision in tissue via cutting element 119 and applies lines of staples on opposing sides of the incision. The simultaneous cutting and stapling avoids complications that may arise when performing such actions sequentially with different surgical tools that respectively only sever and staple. Firing of the staples may be effected by a motor 114 (shown in FIG. 5). Motor 114 distally drives cutting element 119 and the movement of cutting element 119 causes the staples of staple cartridge 110 to be driven through the severed tissue and against the closed anvil 109, which forms or closes the staples to fasten the severed tissue. In an embodiment, stapler 100 may be any suitable motor-driven surgical stapler adapted for use herein such as, for example, the motor-driven surgical stapler shown and described in U.S. Published Application Publication No. 2007/0175962 A1, the contents of which are incorporated by reference herein in their entirety. In another embodiment, stapler 100 or may be a mechanical non-motor driven stapler adapted for use herein such as, for example, the Echelon™60 ENDOPATH® Stapler by Ethicon Endo-Surgery, Inc. When released by the user, firing trigger 121 returns to the open position shown in FIG. 1. Handle portion 102 may include a release button 107 for releasing the locked closure trigger 123.

Figure 5:
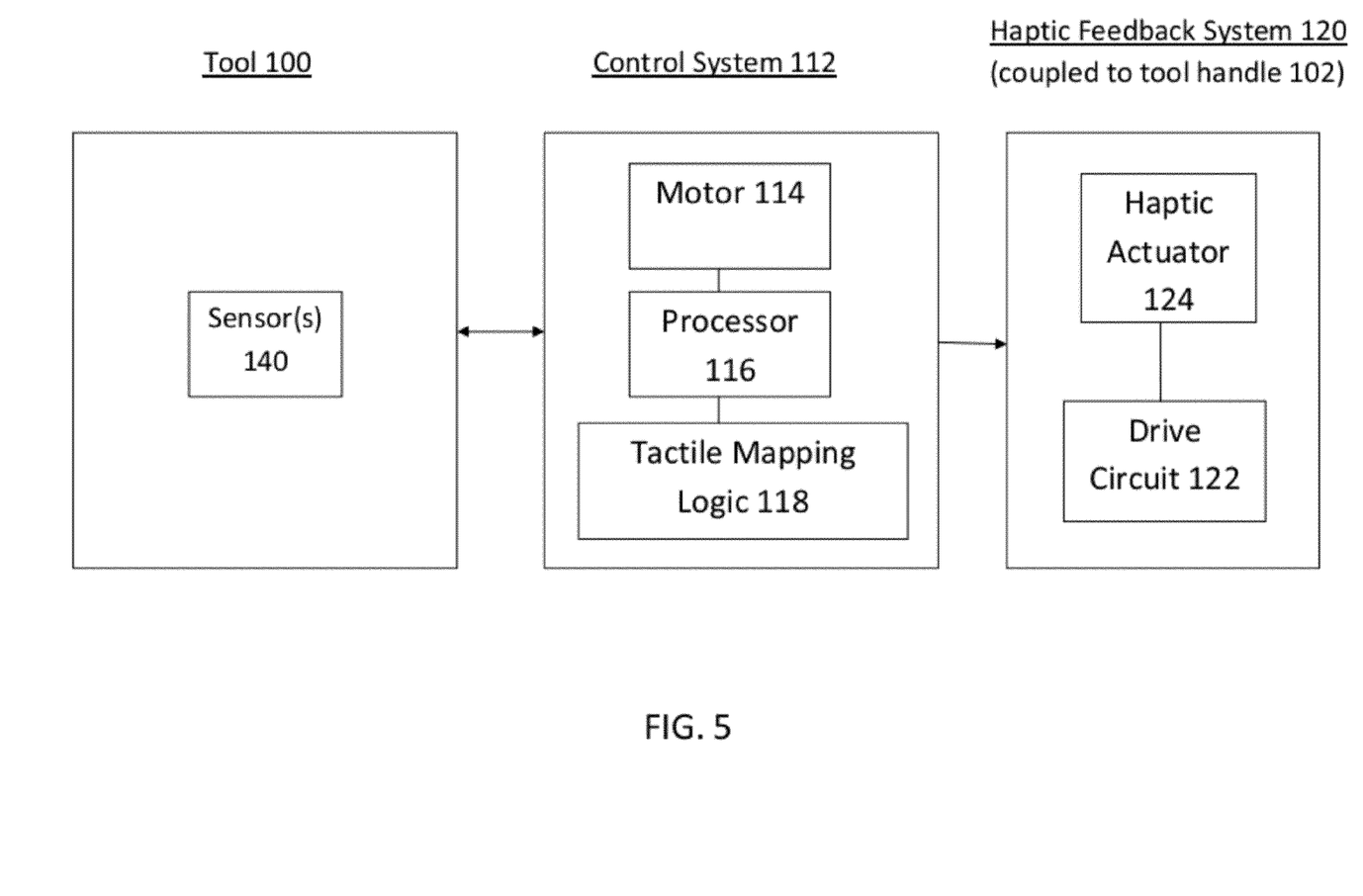
FIG. 5 is a block diagram of the surgical tool system of FIG. 1.

FIG. 5 is a block diagram of surgical tool system 101, further illustrating the relationship between the main components of surgical tool system 101. Control system 112 communicates with one or more sensors 140 coupled to tool 100 as well as handle portion 102 of tool 100 in order to provide haptic effects to the user. More particularly, control system 112 includes a motor 114 for driving cutting element 119, a processor 116 for receiving measurement signals or data from one or more sensors 140 of tool 100 as will be described in more detail herein, and a controller or tactile mapping logic 118 configured to process sensor information from processor 116 into tactile feedback signals or commands. In one embodiment, motor 114, processor 116, and tactile mapping logic 118 are combined into an integral, external component that is separated from stapler 100 and is electrically connected to sensors 140 and haptic feedback system 120 via internal or external wires. Stated in another way, all of the components of control system 112 may be in the same external instrumentation unit. For illustrative purposes only, FIG. 1 illustrates a lead 113 for electrically connecting control system 112 to tool 100 and a lead 117 for electrically connecting control system 112 to tactile feedback system 120. In another embodiment, motor 114, processor 116, and/or tactile mapping logic 118 may be separate external components that are electrically connected together. In yet another embodiment, one or more of motor 114, processor 116, and tactile mapping logic 118 may be mounted within or on handle portion 102 of stapler 100 and are electrically connected to sensors 140 and haptic feedback system 120 via only internal wires. Motor 113 may be provided in handle portion 102 as described, for example, in U.S. Published Patent Application Publication No. 2007/0175962 A1, incorporated by reference herein in its entirety.

As will be explained in more detail herein, sensor(s) 140 may include one or more of a current sensor, an RPM sensor, a displacement or position sensor, and/or a pressure sensor dependent on the desired haptic effects. Processor 116 is electrically connected to sensors 140 via one or more leads or other transmission medium (not shown). During operation of the tool, processor 116 receives data or measurements from sensor(s) 140 and accordingly processes or analyzes the sensor data/measurements as necessary in order to supply the correct type of input to tactile mapping logic 118. Processor 116 may include logic resources, such as a microprocessor, and may further include other specific sensor-dependent components required to analyze and store data/measurements from sensor(s) 140.

Processor 116 outputs the information derived from one or more sensors of tool 100 to tactile mapping logic 118 that further processes the information according to specific algorithms and operator selections. More specifically, tactile mapping logic 118 is configured to map sensed/calculated values derived from the tool sensor(s) onto tactile feedback signals or commands. Mapping may include a function or lookup table, or may include a more complex algorithm, estimation of a system and, if necessary, a finite state machine. Tactile mapping logic 118 determines what haptic effects are to be played and the order in which the effects are played in response to the sensed/calculated values. Tactile mapping logic 118 may be a general-purpose or specific-purpose processing device or microcontroller. In one embodiment, tactile mapping logic 118 may be associated with a memory device (not shown) for storing data and/or instructions. The memory device can be any type of storage device or computer-readable medium, such as random access memory ("RAM") or read-only memory ("ROM"). The memory device stores logical instructions, commands, and/or code executed by tactile mapping logic 118. The memory device may also be located internal to control system 112, or any combination of internal and external memory. In another embodiment, logical instructions, commands, and/or code can be implemented in hardware and incorporated in tactile mapping logic 118 using discrete logic circuitry, an application specific integrated circuit ("ASIC"), a programmable gate array ("PGA"), a field programmable gate array ("FPGA"), etc., or any combination thereof. In yet another embodiment, logical instructions, commands, and/or code can be implemented in both hardware in tactile mapping logic 118 and software/firmware stored in the memory. Although described separately from processor 116, it should be understood by those of ordinary skill in the art that such functional description is for illustrative purposes only and the same instrumentation may be utilized as processor 116 and tactile mapping logic 118.

Tactile mapping logic 118 outputs control signals to haptic feedback system 120 coupled to handle portion 102 of tool 100 to provide feedback information to an operator when performing a procedure. The control signals are communicated via lead or tether 117 (see FIG. 1) that electrically connects tactile mapping logic 118 to haptic feedback system 120. Another lead (not shown) may also be provided between control system 112 and handle portion 102 to provide an isolated ground line for a low voltage actuator circuit located in handle portion 102.

Haptic feedback system 120 includes at least an actuator drive circuit 122 (shown in FIG. 2) which is coupled to a haptic actuator 124 (also shown as FIG. 2) for providing haptic feedback to the operator. In order to provide feedback to the operator, haptic feedback system 120 is electrically connected to control system 112. In one embodiment, in order to communicate commands from tactile mapping logic 118 to haptic actuator 124, control system 112 provides a motor voltage along lead or tether 117 to handle portion 102 of tool 100. As will be explained in more detail herein, haptic actuator 124 may include but is not limited to one or more vibrotactile or kinesthetic actuators that utilize any suitable instrumentation such as but not limited to a friction brake or a dynamic motor coupled to tool 100 for providing the desired haptic effects. As such, tactile mapping logic 118 outputs control signals to drive circuit 122 which includes electronic components and circuitry used to supply haptic actuator 124 with the required electrical current and voltage to cause the desired haptic effects. As mentioned above, a fourth lead (not shown) may also be provided between control system 112 and handle portion 102 to provide an isolated ground line for a drive circuit 122 in handle portion 102 such that tactile mapping logic 118 communicates with haptic feedback system 120 via an isolated DC voltage line having two conductors.

Haptic feedback may be generated and provided to the user, including vibrotactile, kinesthetic, handle deformation and/or other types of tactile feedback such as texture and heat. Haptic actuators 124 may include electromagnetic motors, eccentric rotating mass ("ERM") actuators in which an eccentric mass is moved by a motor, linear resonant actuators ("LRAs") in which a mass attached to a spring is driven back and forth, shape memory alloys, electro-active polymers that deform in response to signals, mechanisms for changing stiffness, vibrotactile actuators, inertial actuators, piezoelectric actuators, or other suitable types of actuating devices. In one embodiment, haptic actuator 124 can be implemented as an inertial actuator to provide vibrotactile feedback to the operator. In another embodiment, kinesthetic haptic feedback may utilize, for example, solenoids to change the stiffness/damping of handle portion 102, small air bags that change size in handle portion 102, or shape changing materials. A detailed description of drive circuits and haptic actuators suitable for use herein may be found in U.S. patent application Ser. No. 11/862,639, filed Sep. 28, 2007, herein incorporated by reference in its entirety.

In one embodiment, haptic actuator 124 is a vibrotactile device that generates vibrations on handle portion 102 for haptic feedback. For example, in one embodiment, one or more vibrotactile actuators may be incorporated in handle portion 102 at several locations corresponding to the palm, fingers, and/or thumb of a hand of the surgeon for providing high bandwidth vibrotactile feedback over the entire handle. A target acceleration of between 4-5 G's at resonance is desirable, along with response greater than 2.5 G's from 100-250 Hz, although it will be understood by those of ordinary skill in the art that much less capable haptic displays are also valuable. In one embodiment, all moving mass components relating to actuation of haptic actuator 124 are internal to tool 100.

In another embodiment, haptic actuator 124 is a kinesthetic device such as a friction brake or a motor that enables variable resistance to motion, lock-out, barrier and detent display on handle portion 102 for haptic feedback. For example, in one embodiment, firing trigger 121 for cutting and stapling tissue and/or closure trigger 123 for clamping tissue may be fitted with a kinesthetic actuation means to enable kinesthetic haptic effects. In addition, one or more kinesthetic actuators may be incorporated in handle portion 102 at several locations corresponding to the palm, fingers, and/or thumb of a hand of the surgeon for providing resistance of motion to the entire grasper portion of the handle. The kinesthetic actuators may be capable of at least significantly impeding motion but also be capable of displaying detents. For example, in one embodiment, the kinesthetic actuators may have a resistance of between 20% and 30% of the maximum applied force in order to display effective impeding forces. In another embodiment, the kinesthetic actuators may be capable of impeding all user motion to communicate a "lock-out" mode.

As previously mentioned, the type of tool sensor(s) as well as the operation of processor 116 depends on desired haptic effects. In one embodiment depicted in FIG. 6, tactile feedback system 120 relates to tissue anisotropy to alert the user of the presence of unusual structures located within the jaws of tool 100. During a surgical procedure utilizing a surgical stapler, visual occlusion prevents the user from clearly seeing all structures that are within the jaws of the stapler. In addition, automated firing systems and/or high mechanical advantage remove the tactile component of staple firing such that the user is not aware of what type of structures may be stapled together. Certain targets that should not be stapled, such as scar tissue, a bougie, or a NG tube, may be inadvertently clamped within the jaws of tool 100. Accordingly, in one embodiment, tool 600 includes a sensor 640 coupled to tool 600 and a tissue-anisotropy processor or algorithm 616 in the control system. In one embodiment, sensor 640 may be a current sensor coupled to motor 114 such as but not limited to a current sensor manufactured by Silicon Labs of Austin, Tex. In another embodiment, sensor 640 is an optical encoder disk coupled to motor 114 that is utilized for calculating RPM of motor 114. In yet another embodiment, sensor 640 is a pressure sensor coupled to the jaws of stapler 600 for directly measuring the pressure distribution along the jaw members. Suitable pressure sensors for measuring pressure distribution are described in U.S. patent application Ser. No. 11/955,563, filed Dec. 13, 2007, herein incorporated by reference in its entirety. Tissue-anisotropy processor 616 continuously receives measurement signals from sensor(s) 640 and calculates/estimates the type of tissue or other structure being cut within the jaws of tool 600 by leveraging the information sensed from motor 114 during cutting and/or by leveraging the sensed pressure distribution from the stapler jaws. Tactile mapping logic 118 utilizes an algorithm to map the sensor data into haptic commands for haptic feedback system 120. The algorithm may include for example straight mapping of the sensed/calculated sensor information to amplitude, partial mapping using spectral filtering into a spread-spectrum haptic signal, digital filtering of the sensed/calculated sensor information into haptic signal, or thresholding of the sensed/calculated sensor information to provide alerts.

Figure 6:
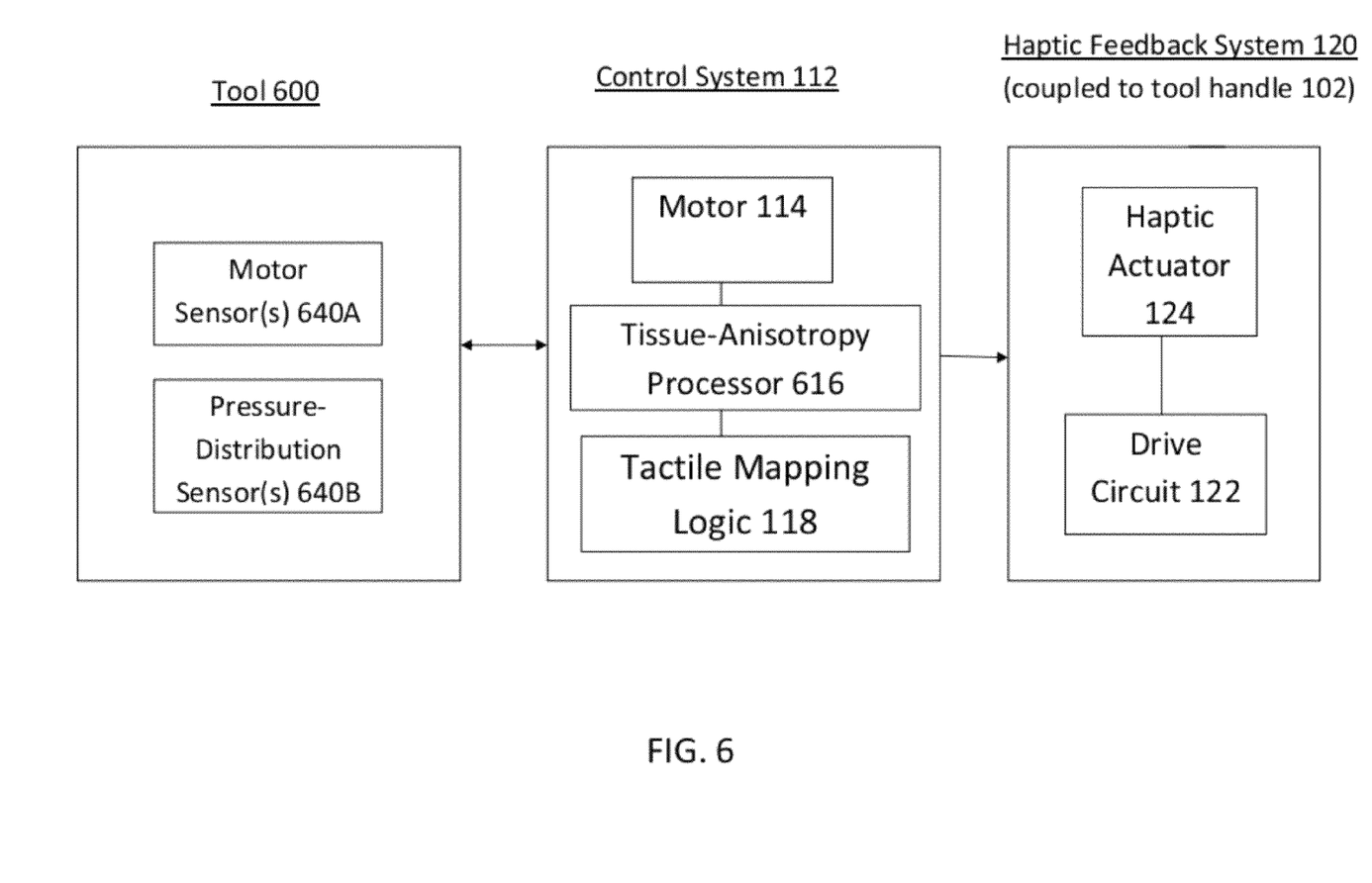
FIG. 6 is a block diagram of a surgical tool system according to an embodiment hereof in which haptic effects relating to tissue anisotropy are communicated to the user.

Based on the measurement signals from sensor 640, tissue anisotropy feedback may be provided to the user. Haptic feedback alerts may be provided to the user as sensor measurements cross through several thresholds, or may be provided to the user if the measurements indicate an unusual structure in the jaws of the device. For example, the feedback may include a continuous real-time vibrotactile display of the sensed/calculated sensor information as the sensor measurements pass through preset thresholds or in the form of an amplified tactile texture felt by the user as the cutting element progresses. In another embodiment, a negative valence vibrotactile alert may be given if the tissue/structure within the device is not appropriate to be stapled or cut, and a positive valence vibrotactile alert may be given if the tissue/structure within the device is appropriate to be stapled or cut. In addition, haptic effects may include a kinesthetic lock-out or variable-magnitude barrier on firing trigger 121 and/or closure trigger 123 to prevent the user from cutting and stapling and/or clamping down onto the tissue, respectively. In addition, haptic feedback may be provided in different modes such as a training mode and an experienced mode in order to accommodate the needs of users having varying degrees of experience with the tool. The lock-out may be provided if tool 100 is being operated in a training mode, while the variable-magnitude barrier may be provided if tool 100 is being operated in an experienced mode.

Figure 7:
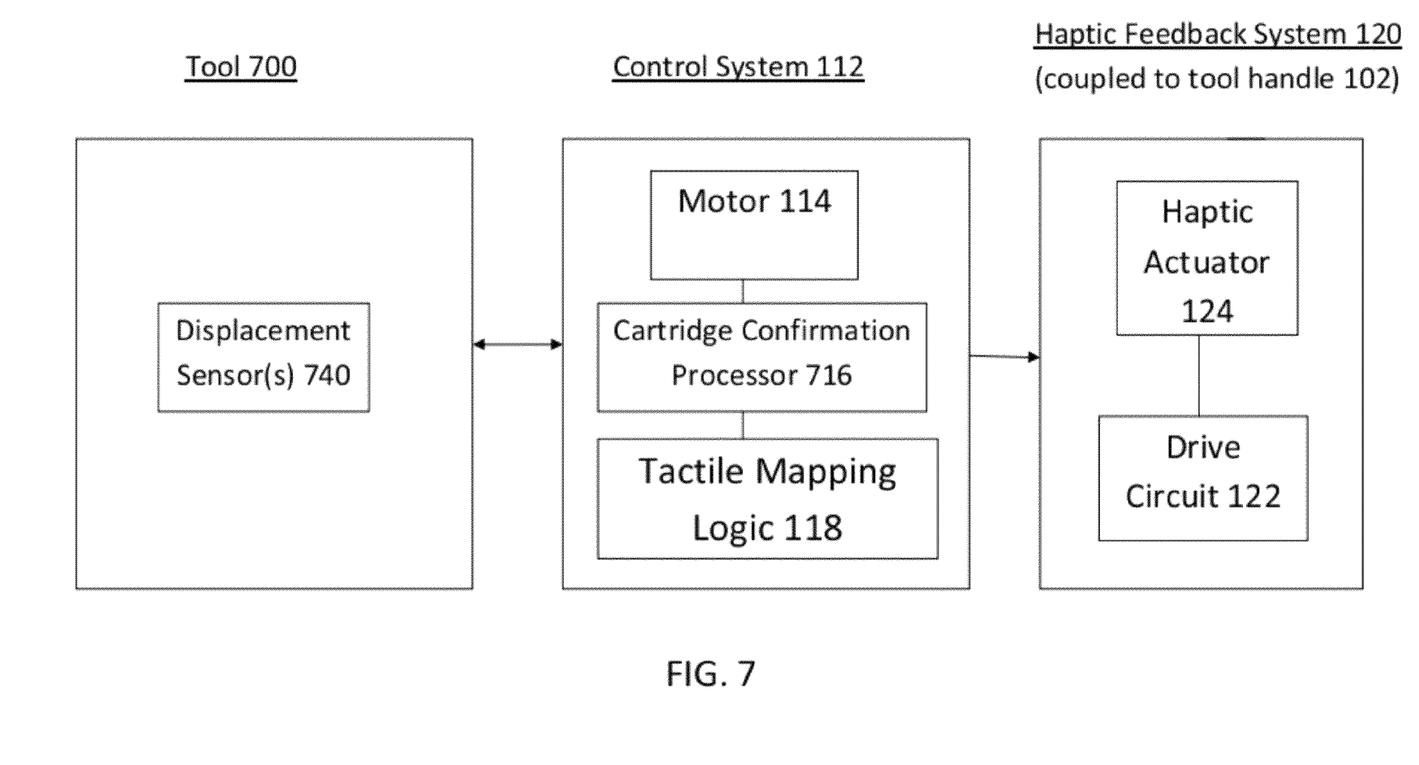
FIG. 7 is a block diagram of a surgical tool system according to an embodiment hereof in which haptic effects relating to the quantity or thickness of tissue within the jaws of the surgical tool and confirmation of the staple cartridge selection are communicated to the user.

In another embodiment shown in FIG. 7, tactile feedback system 120 alerts the tool user of the quantity/thickness of tissue located within the jaws of tool 100 to alert the user if an inappropriate amount of tissue is being stapled for the selected cartridge. Stapling cartridges are typically rated for a range of tissue and/or blood vessel thickness and users should be alerted when the amount of tissue clamped within jaw members 108, 109 does not fall within the range. On one end of the tissue-quantity spectrum, a sufficient amount of tissue should be captured between the jaws of the stapler to ensure that the stapler can staple the tissue. If not enough tissue is located within the jaws for a particular stapler cartridge, the jaws may be drawn too close together, especially pinching at their distal ends, and thus the stapler may not effectively form closed staples in the severed tissue. At the other end of the spectrum, an excessive amount of clamped tissue may cause binding and an incomplete firing of the staples. Tool 700 includes a displacement sensor 740 coupled to the distal end of tool 700 and a cartridge-confirmation processor 716 in the control system. Jaw displacement may be measured with a potentiometer or other suitable position encoder on the hinge of the jaw members. In one embodiment, control system 112 detects the type/size of stapler cartridge inserted in the stapler using a suitable sensing means so that the calculations performed by processor 716 are consistent with the cartridge selected for use. In another embodiment, the user inputs or selects a type/size of stapler cartridge into a graphic user interface (GUI) so that the calculations performed by processor 716 are consistent with the cartridge selected for use. Cartridge-confirmation processor 716 continuously monitors displacement/position measurements received from sensor 740, and calculates/estimates the amount of tissue located within the jaws of tool 700 from the displacement/position measurements to determine if stapling in the current clamped configuration will result in incomplete staple formation.

If processor 716 indicates that the amount of tissue within the jaws of the stapler is not appropriate for the stapler cartridge, tissue quantity feedback may be provided to the user. For example, a negative valence vibrotactile alert may be given if the amount of tissue within the device is not appropriate to be stapled or cut, and a positive valence vibrotactile alert may be given if the amount of tissue within the device is appropriate to be stapled or cut. In addition, haptic effects may include a kinesthetic barrier on firing trigger 121 to prevent the user from cutting and stapling the tissue. Haptic feedback may be provided in different modes such as a training mode and an experienced mode in order to accommodate the needs of users having varying degrees of experience with the tool. In one embodiment, the kinesthetic barrier has an initial magnitude that may be overcome by the user, which triggers a negative valence vibrotactile alert and then a higher magnitude kinesthetic barrier. The second kinesthetic barrier may be overcome if the tool is being operated in an experienced mode such that firing of the staples occurs, or a lock-out kinesthetic barrier may be provided if the tool if being operated in a training mode.

Figure 8:
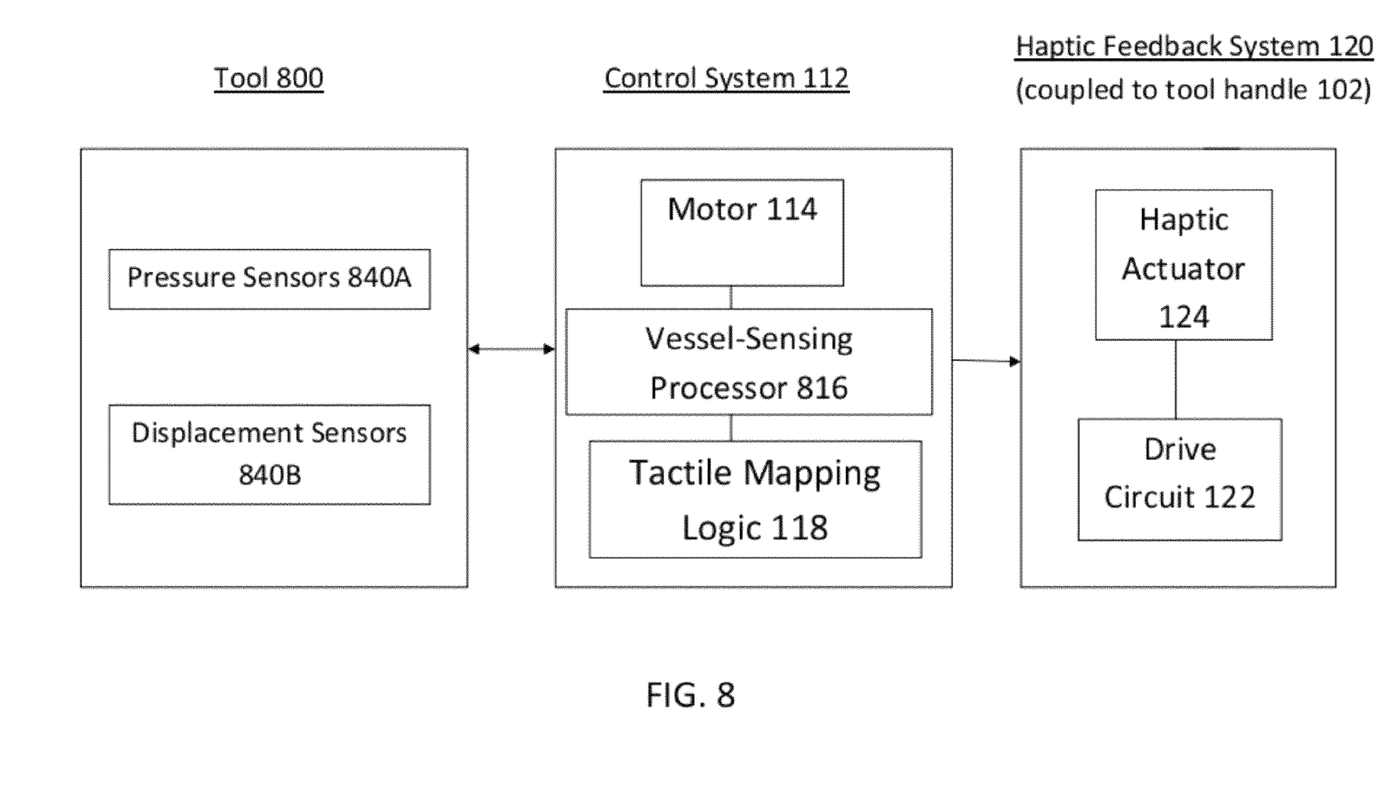
FIG. 8 is a block diagram of a surgical tool system according to an embodiment hereof in which haptic effects relating to vessel-sensing within the jaws of the surgical tool are communicated to the user.

In yet another embodiment shown in FIG. 8, tactile feedback system 120 alerts the tool user of the presence of vascular tissue located within the jaws of the surgical tool. The user is notified if there are vascular structures beyond a threshold diameter within the jaws, and more importantly, the user is notified if there is vascular tissue that is not completely within the jaws or not well oriented in the jaws. Tool 800 includes one or more pressure sensors 840A and one or more displacement sensors 840B coupled to the distal end of the tool, and a vessel-sensing processor 816 in the control system. Jaw displacement may be measured with a potentiometer or other suitable position encoder on the hinge of the jaw members. Pressure sensing is most effectively achieved with a capacitive pressure sensor array such as those made by pressure profile systems. Vessel-sensing processor 816 continuously monitors pressure and displacement measurements received from sensors 840A, 840B, respectively, and interprets pressure/pulsation data to determine if a blood vessel extends beyond distal tip of device. Detailed description of possibly suitable sensors and methods for detection of a blood vessel with a minimally invasive tool suitable for use herein may be found in U.S. Patent Publication 2010/0179423, filed Jan. 15, 2009; U.S. Patent Publication 2010/0137845, filed Dec. 3, 2008; U.S. Patent Publication 2010/0152586, filed Dec. 12, 2008; U.S. Patent Publication 2010/0179587, filed Jan. 15, 2009, each of which is herein incorporated by reference in its entirety. Haptic feedback for vessel-sensing may include both vibrotactile and kinesthetic effects. For example, in order to warn a user that a blood vessel is only partially within the jaws of tool 800, haptic effects may include a kinesthetic lock-out or high-magnitude barrier on trigger 121 to prevent cutting of the tissue. In another embodiment, a negative valence vibrotactile alert may be given if the vascular structure is only partially within the jaws of the device.

In another embodiment, pressure sensors 840A, displacement sensors 840B, and vessel-sensing processor 816 may also be utilized to alert the tool user of whether the stapling process has successfully sealed the tissue located within the jaws of the stapler. It is essential for the user to know if the tissue has been sealed by the staples because the user should not release the clamped tissue from the jaws of the stapler prior to adequate sealing. Detection of adequate sealing can prevent a catastrophic bleed which can occur if a less than adequately sealed vessel is unclamped. More particularly, vessel-sensing processor 816 may utilize measurement signals from pressure sensor(s) 840A and displacement sensor(s) 840B to determine if vessel pulsatility, i.e., a patent lumen, still exists on both sides of the seal prior to releasing the clamped tissue. If tissue is sealed after stapling is completed, there is no blood flow/pulsation through the blood vessel. Haptic feedback for sealing completeness may include both vibrotactile and kinesthetic effects. For example, in order to warn a user that the tissue is not completely sealed, haptic effects may include a kinesthetic lock-out or high-magnitude barrier on release button 107 to prevent unclamping of the tissue. In another embodiment, a negative valence vibrotactile alert may be given if the tissue is not completely sealed.

In yet another embodiment, pressure sensors 840A, displacement sensors 840B, and vessel-sensing processor 816 may also be utilized to alert the tool user of the length of tissue located within the jaws of tool 100 to alert the user if an inappropriate length of tissue is being stapled for the selected cartridge. Stapling cartridges may be provided in particular lengths and users should be alerted when the length of tissue clamped within jaw members 108, 109 does not fall within the range. More particularly, it is desirable to know how much of the jaw members are covered with tissue because staples should only be fired where tissue is present. Thus, if tissue only covers a proximal portion of the jaw length, the user does not want to fire staples within the distal portion of the jaw length because such staples would be fired into a body lumen rather than into tissue. A user should select a staple cartridge having the appropriate length or number of staples to ensure that the staples are only fired where tissue is present. In one embodiment, control system 112 detects the length of stapler cartridge inserted in the stapler using a suitable sensing means so that the calculations performed by processor 816 are consistent with the cartridge selected for use. In another embodiment, the user inputs or selects a length of stapler cartridge into a graphic user interface (GUI) so that the calculations performed by processor 816 are consistent with the cartridge selected for use. Processor 716 continuously monitors displacement and/or pressure measurement signals received from pressure sensors 840A and displacement sensors 840B, respectively, and calculates/estimates the length of tissue located within the jaws of tool 800 to determine if the staple cartridge length is appropriate for the clamped tissue. If processor 816 indicates that the length of tissue within the jaws of the stapler is not appropriate for the stapler cartridge, tissue quantity feedback may be provided to the user. For example, a negative valence vibrotactile alert may be given if the length of tissue within the device is not appropriate to be stapled or cut, and a positive valence vibrotactile alert may be given if the length of tissue within the device is appropriate to be stapled or cut. In addition, haptic effects may include a kinesthetic barrier on firing trigger 121 to prevent the user from cutting and stapling the tissue. Haptic feedback may be provided in different modes such as a training mode and an experienced mode in order to accommodate the needs of users having varying degrees of experience with the tool. In one embodiment, the kinesthetic barrier has an initial magnitude that may be overcome by the user, which triggers a negative valence vibrotactile alert and then a higher magnitude kinesthetic barrier. The second kinesthetic barrier may be overcome if the tool is being operated in an experienced mode such that firing of the staples occurs, or a lock-out kinesthetic barrier may be provided if the tool if being operated in a training mode.

Figure 9:
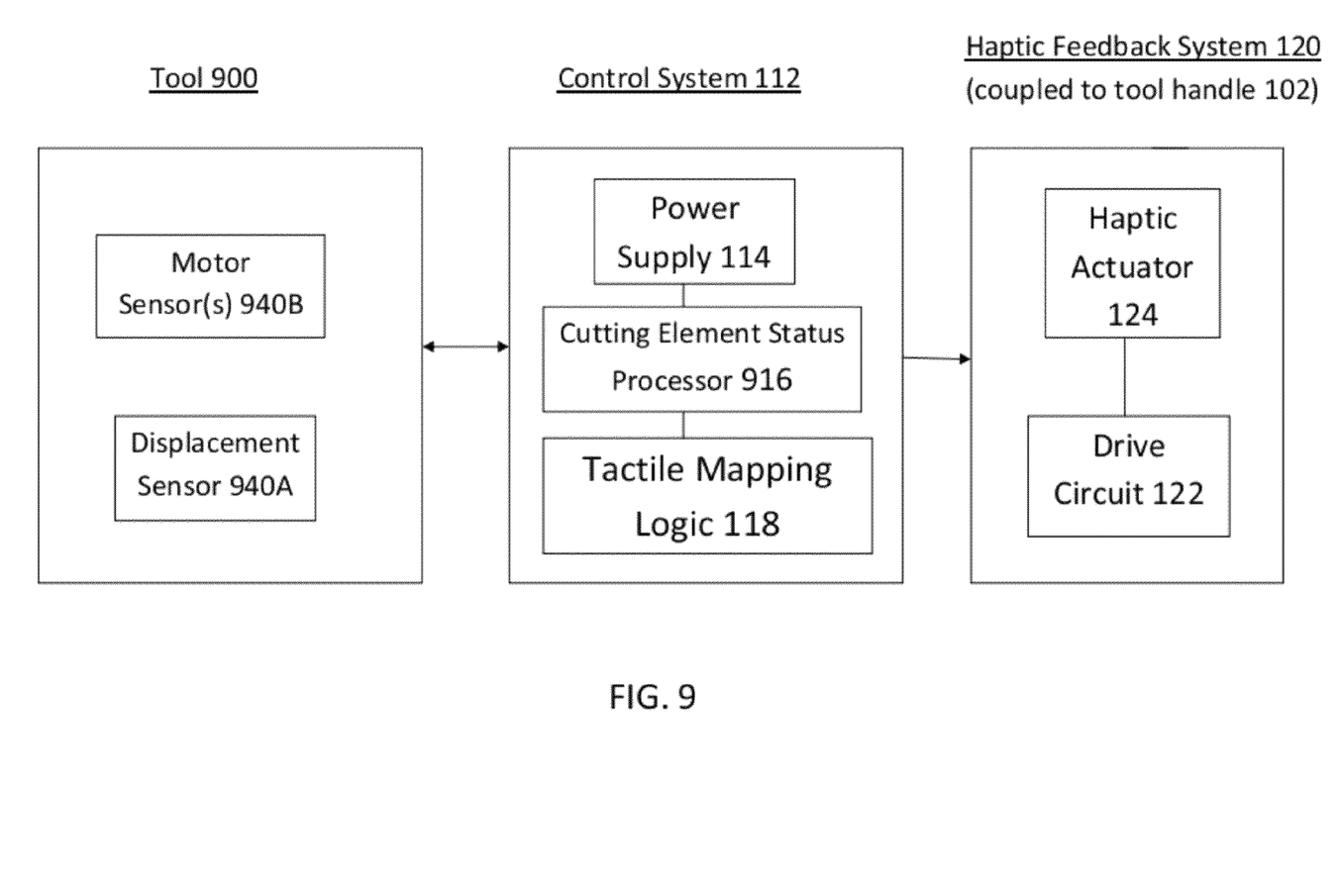
FIG. 9 is a block diagram of a surgical tool system according to an embodiment hereof in which haptic effects relating to the status of the cutting element are communicated to the user.

In another embodiment shown in FIG. 9, tool 900 includes a displacement sensor 940A which is capable of measuring displacement of cutting element 119, and a cutting element status processor 916 for alerting the user of the state of cutting element 119 during the stapling procedure. In one embodiment, in order to determine and/or verify position of cutting tool 119, tool 900 may also include a motor sensor 940B. In one embodiment, motor sensor 940B may be a current sensor coupled to motor 114 such as a current sensor manufactured by Silicon Labs of Austin, Tex. In another embodiment, motor sensor 640 is an optical encoder disk or other suitable speed measuring sensors that is utilized for calculating RPM of motor 114. Displacement sensor 940 is coupled to cutting element 119 to provide information relating to the position of cutting element 119. Displacement sensor 940 may be a position encoder mounted to the shaft of the drive motor, a linear potentiometer or LVDT, or other sensor suitable for obtaining position data of cutting element 119. Displacement sensor 940A and/or motor sensor 940B continuously provides information to processor 916 such that processor 916 determines the position of cutting element 119.

In one embodiment, the position of cutting element 119 may be utilized to provide an indication of when the tissue-stapling cycle or treatment is complete. The completion of the tissue-stapling cycle needs to be indicated to the user to enable them to proceed with the surgery, which may include the steps of initiating another firing cycle, repositioning the stapler, and/or removing the stapler. When cutting element 119 reaches its most distal location that signifies that the firing cycle is complete, tactile feedback system 120 provides haptic effects to the user. In one embodiment, the haptic effects may be a single haptic alert such as a vibrotactile alert to indicate completion of the tissue-stapling cycle. In another embodiment, the haptic effects may include continuous feedback based on live position values as the cutting element 119 advances longitudinally in a distal direction such as a vibrotactile feedback with a sequence of increasing amplitudes. It will be understood by those of ordinary skill in the art that haptic effects may include both alerts and continuous feedback.

In yet another embodiment, tactile mapping logic 118 may output command signals to motor 114. For example, when the position of cutting element 119 indicates that tissue stapling is complete, tactile mapping logic 118 may output a command signal to shut down motor 114, thereby preventing additional tissue-cutting and controlling the behavior of the stapler.

In addition to haptic effects relating to the position of cutting element 119, haptic feedback relating tissue properties of the tissue being cut may also be provided during the cutting procedure. For example, passive kinesthetic resistance may be provided on trigger 121 and/or on handle grip 105. The kinesthetic resistance during motion of cutting element 119 may be a function of sensed tissue properties. For example, the kinesthetic resistance may be varied according to stiffness of the tissue being cut, which may be sensed via a strain gauge or other suitable sensor at the distal tip of the tool. A more detailed description of monitoring tissue properties such as stiffness and providing haptic effects relating thereto may be found in U.S. patent application Ser. No. 11/955,563, filed Dec. 13, 2007, previously incorporated by reference in its entirety.

Embodiments described above relate to various conditions that may be monitored and communicated to the user in the form of haptic effects. Although haptic effects for tissue anisotropy, cartridge confirmation, vessel-sensing, and cutting element position are each described separately herein, it will be understood by those of ordinary skill in the art that a surgical stapling tool may incorporate any combination of the above-described embodiments. In addition, a single processor of a surgical stapling tool including one or more of the above-described embodiments may be configured to receive input/measurements from various sensor devices and perform the required tasks or calculations thereon.

As described herein, a positive valence or negative valence alerts may be utilized in various situations to indicate proper or improper use, respectively, of the stapler. A pulsing vibrotactile error alert may be utilized to ensure compliance with all proper instructions for use of tool 100, including sensed improper uses as described herein or other programmable improper uses such as time periods or sequence of steps. In one embodiment, the vibrotactile error haptic effect may be the same for all error states but may include a follow-on haptic, audible, or visual effect that will provide more information about the specific error state to users. These follow on effects may include additional haptic pulses with user discernable envelopes to indicate different conditions. Alternately, the error effect could be displayed with different temporal spacing depending on the severity of the condition. In another embodiment, the positive or negative valence alerts may be played for a fixed duration following the alert condition, which in some circumstances may continue past the time when the knife has returned to its resting position.

Figure 10:
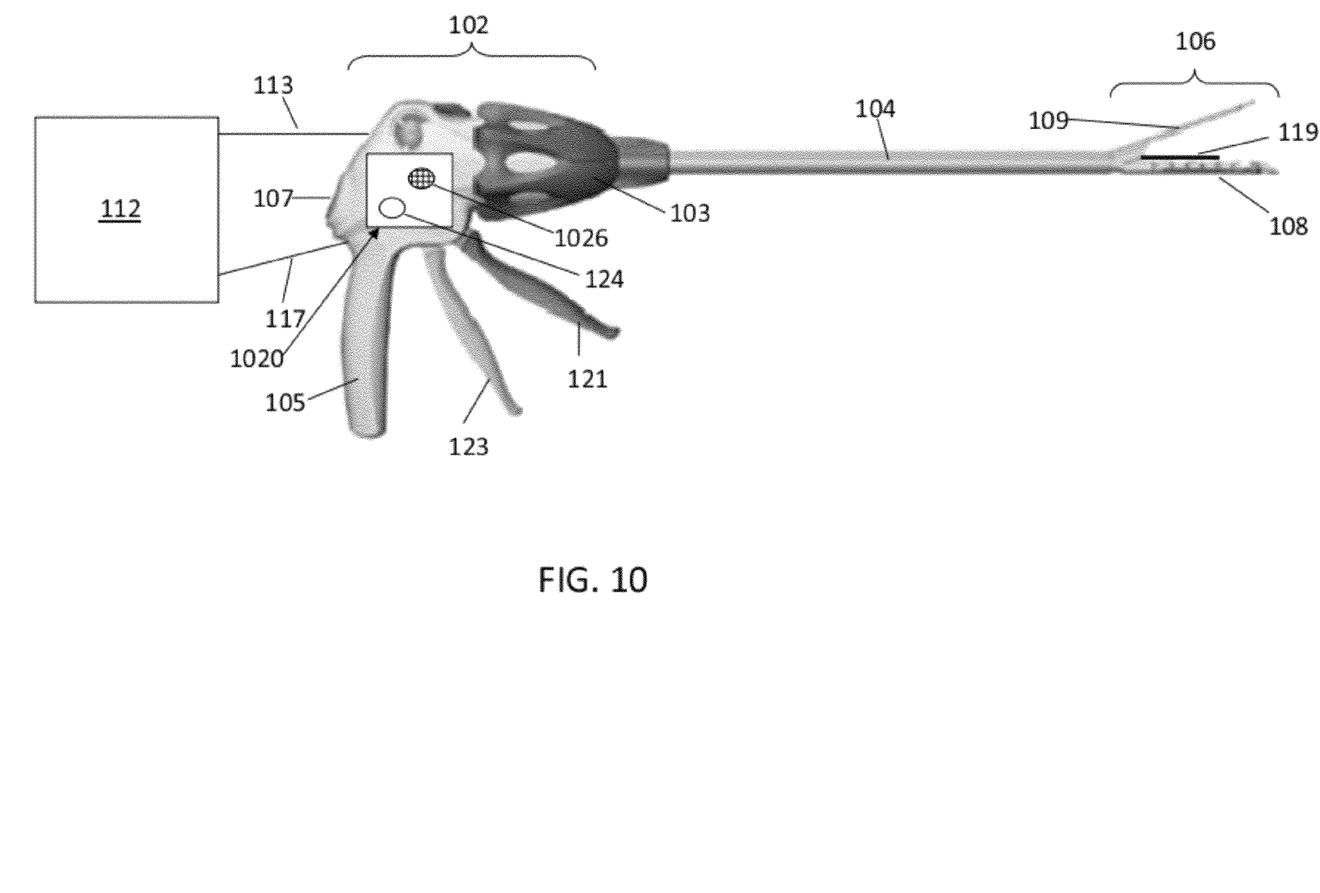
FIG. 10 is a diagram illustrating a side view of a surgical tool system having haptic and audio feedback mechanisms, according to an embodiment hereof.

For example, referring to FIG. 10, an embodiment incorporating two types or modes of feedback for the operator is shown. Specifically, haptic feedback system 1020 provides both haptic and audio feedback via haptic actuator 124 and an audio device or speaker 1026. Tactile mapping logic 118 communicates the processed information to one or more of haptic actuator 124 and audio device 1026 according to which ones of these feedback mechanisms are enabled and how they are controlled to provide their respective outputs. In one embodiment, feedback may be provided to the operator in a continuous manner as the operator performs the surgery. In another embodiment, feedback may be provided to the operator as an alert to notify or warn the operator when a particular condition is satisfied. Further, one type of feedback (i.e., haptic or audio) may be provided in a continuous manner while another type of feedback is provided as an alert.

Figure 11:
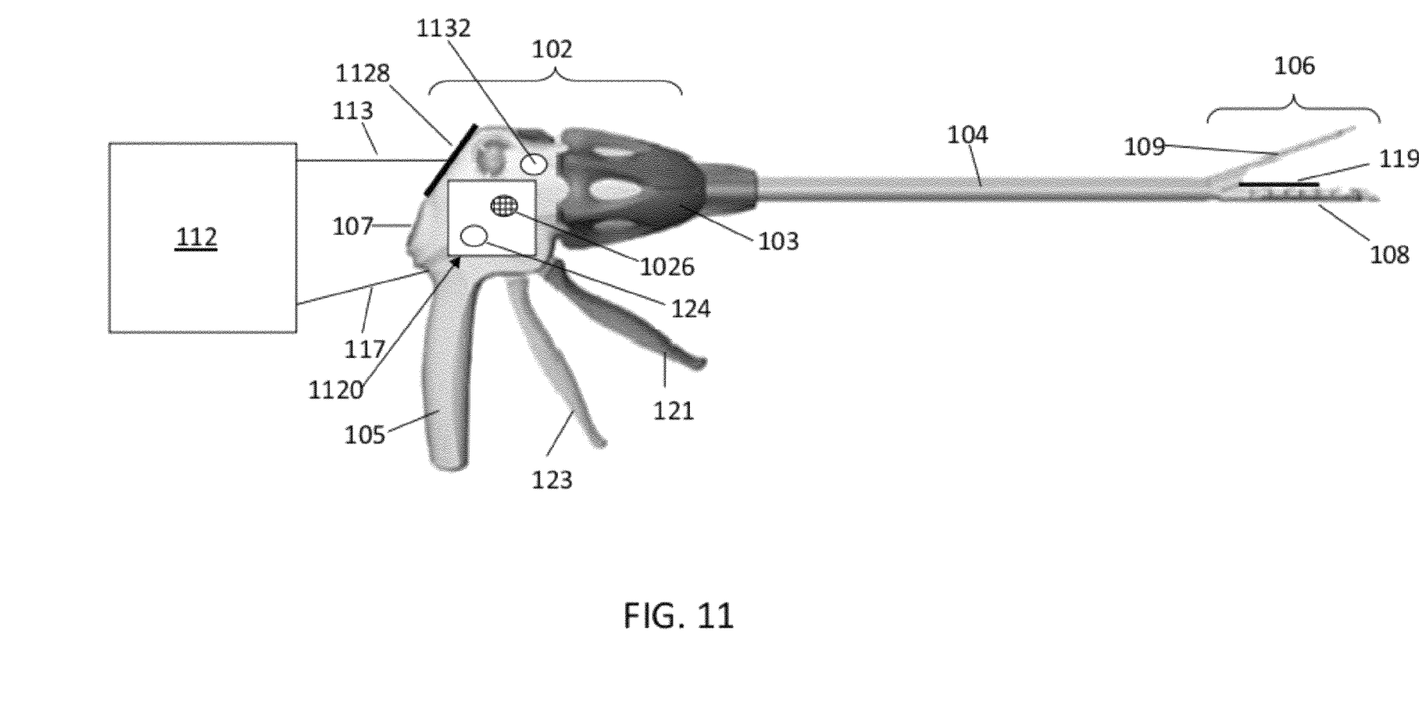
FIG. 11 is a diagram illustrating a side view of a surgical tool system having haptic, audio, and visual feedback mechanisms, according to another embodiment hereof.

Referring to FIG. 11, an embodiment incorporating three types or modes of feedback for the operator is shown. Specifically, haptic feedback system 1120 provides haptic, audio, and visual feedback via haptic actuator 124, audio device or speaker 1026, and visual display 1128, respectively. Tactile mapping logic 118 communicates the processed information to one or more of haptic actuator 124, audio device 1026, visual display 1128 according to which ones of these feedback mechanisms are enabled and how they are controlled to provide their respective outputs. In this embodiment, visual display 1128 is a liquid crystal display (LCD) screen on a back region of handle portion 102. In another embodiment, visual display 1128 may be incorporated into the camera monitor display of the laparoscope so that the visual feedback is always within the user's line or sight. In one embodiment, an ultrasound transducer (not shown) may be coupled to distal portion 106 of tool 100 and visual display 1128 may be configured to show ultrasound image information to assist the surgeon to position the tool as needed. Visual display 1128 can include a touch screen, which can be configured to present information to the operator and can also be configured to sense when the operator presses certain portions of the touch screen. In this way, the touch screen can act as a touchable user interface with graphical presentation capabilities. Visual display 1128 may include a graphical user device that enables the surgeon to select different feedback profiles, adjust sensor behavior, modify supplemental information, and the like.

According to the embodiment of FIG. 11, the handle portion of the surgical tool may further include one or more buttons 1132. Buttons 1132 can be configured using any suitable mechanism for allowing an operator to control the nature of the feedback that is provided to the operator. Buttons 1132 may include devices for allowing certain levels, intensities, or amplitudes to be adjusted or certain selections to be made regarding the output presented to the operator. In some embodiments, buttons 1132 may be configured as switches, such as momentary toggle switches, allowing an operator to select different ways in which sensor information is mapped or provided to respective output devices. Buttons 1132 can be implemented as a rocker switch or as a one-dimensional control surface. According to one function of buttons 1132, the operator can enable or disable one or more output mechanisms by controlling whether or not output signals based on the sensed signals are provided to the respective output devices. Another function of buttons 1132 includes the ability to enable one or more output mechanisms. In this regard, the operator can control if and how feedback is presented in a visual, auditory, and/or haptic fashion. With feedback tailored to the surgeon's preferences, the tool can provide feedback to supplement the operator experience for better operation and performance.

It will be apparent to those of ordinary skill in the art that embodiments hereof relate to any type of tools that can be manipulated by an operator. More particularly, the tools described in the present disclosure include a handle portion that mechanically controls a distal portion of the tool. According to embodiments hereof, one or more sensor(s) located on the surgical tool and a haptic feedback system may collectively function to extract pertinent information regarding the operating status of the tool that is subsequently communicated to the operator as haptic, audio, and/or visual feedback. Although embodiments disclosed are tools for laparoscopic surgery, other embodiments can be used for non-laparoscopic surgeries such as in vascular or other catheterization where information detected from a sensor on the tool-tip can be communicated back to the catheter handle. Further, for endoscopy procedures, information detected from a sensor on a flexible endoscope can be communicated back to the endoscope handle. Other embodiments can be used for telesurgery or telepresence in order to, for example, perform routine external examinations and/or utilize open surgical tools by a remote doctor. Another embodiment is the inclusion of this type of feedback in robotic surgical systems, such as the da Vinci® Surgical System of Intuitive Surgical, Inc., to enable operators to have direct tactile feedback.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A surgical tool system comprising:
    a surgical tool operable to staple tissue, the tool including a distal portion including a tissue stapling mechanism connected to a handle via a shaft;
    a sensor coupled to the surgical tool, wherein the sensor is configured to monitor a tissue property;
    a control system electrically connected to sensor, wherein the control system calculates sensor information from signals received from the sensor and processes the sensor information into signal commands;
    a cutting element on the distal portion of the tool;
    a displacement sensor coupled to two opposing jaw members at the distal portion of the tool;
    a firing trigger coupled to the cutting element and the stapling mechanism; and
    a feedback system including one or more haptic actuators coupled to the handle and electrically connected to the control system, wherein the control system communicates the signal commands to the feedback system and the feedback system uses the signal commands to generate haptic feedback relating to the sensor information to the handle,
    wherein the feedback system is configured to generate haptic feedback informing a user of the thickness of tissue located within the two opposing jaw members based on information from the displacement sensor, and
    wherein the one or more haptic actuators include a kinesthetic actuator coupled to the firing trigger to enable variable resistance to motion as the haptic feedback.

2. The surgical tool system of claim 1, wherein the sensor is selected from a group consisting of a current sensor coupled to a motor for driving the tissue stapling mechanism, an RPM sensor coupled to a motor for driving the tissue stapling mechanism, and a pressure distribution sensor coupled to the two opposing jaw members coupled to the distal portion of the tool and the haptic feedback generated by the feedback system informs a user of tissue anisotropy.

3. The surgical tool system of claim 1, wherein the sensor is coupled to the distal portion of the tool and is a pressure sensor and wherein the feedback system is adapted to generate the haptic feedback informing the user that a vessel is only partially located within two opposing jaw members coupled to the distal portion of the tool.

4. The surgical tool system of claim 1, wherein the sensor is coupled to the distal portion of the tool and is a pressure sensor and wherein the feedback system is adapted to generate the haptic feedback informing the user that a vessel is completely sealed by the tissue stapling mechanism.

5. The surgical tool system of claim 1, wherein the sensor is coupled to the distal portion of the tool and is selected from the group consisting of a pressure sensor and a displacement sensor and wherein the feedback system is adapted to generate the haptic feedback depending on the length of tissue located within two opposing jaw members coupled to the distal portion of the tool.

6. The surgical tool system of claim 1, further comprising a cutting element displacement sensor coupled to the cutting element, and wherein the feedback system is adapted to generate the haptic feedback informing a user of the position of the cutting element.

7. The surgical tool system of claim 6, wherein the haptic feedback system is adapted to generate the haptic feedback informing the user upon completion of the stapling procedure.

8. The surgical tool system of claim 1, wherein the haptic feedback generated by the feedback system includes at least vibratory or kinesthetic feedback.

9. The surgical tool system of claim 1, wherein the control system is adapted to vary the signal commands depending on a selected mode based on a user's level of experience such that the generated haptic feedback varies depending on the selected mode.

10. The surgical tool system of claim 1, further comprising:
    a cartridge-confirmation processor adapted to continuously monitor displacement measurements received from the displacement sensor and to calculate the amount of tissue located within the two opposing jaw members from the displacement measurements to determine if stapling in the current clamped configuration will result in incomplete staple formation,
    wherein the cartridge-confirmation processor is adapted to control the kinesthetic actuator to provide a kinesthetic barrier on the firing trigger to prevent the user from cutting and stapling the tissue if the amount of tissue within the two opposing jaw members is detected as being inappropriate for a selected stapler cartridge.

11. A method of providing feedback to a user during a tissue stapling surgical procedure, the method comprising the steps of:
    monitoring a tissue property during the tissue stapling surgical procedure via at least one sensor mounted on a distal portion of a surgical tool, wherein the tissue property is thickness;
    processing the sensor information; and
    communicating haptic feedback to a handle of the surgical tool, wherein the haptic feedback relates to the sensor information and informs a user that an inappropriate amount of tissue is located within two opposing jaw members coupled to the distal portion of the tool,
    wherein the haptic feedback includes a variable resistance to motion to a firing trigger disposed at the handle that causes a stapling mechanism of the tool to activate.

12. The method of claim 11, further comprising the step of monitoring a second tissue property during the tissue stapling procedure, wherein the second tissue property is tissue anisotropy and the haptic feedback informs the user of structures located within two opposing jaw members coupled to the distal portion of the tool.

13. The method of claim 11, wherein the haptic feedback is a kinesthetic lock-out that prevents the user from squeezing the trigger to activate the stapling mechanism if an inappropriate amount of tissue is located within the two opposing jaw members coupled to the distal portion of the tool.

14. The method of claim 11, further comprising the step of monitoring a second tissue property during the tissue stapling procedure, wherein the second tissue property is vessel sensing and the haptic feedback informs the user that a vessel is only partially within the two opposing jaw members coupled to the distal portion of the tool.

15. The method of claim 11, wherein the tissue property is length and the haptic feedback informs a user that an inappropriate length of tissue is located within two opposing jaw members coupled to the distal portion of the tool.

16. The method of claim 11, wherein the tissue property is pulsatility and the haptic feedback informs a user if the tissue is located within two opposing jaw members coupled to the distal portion of the tool is sealed.

17. The method of claim 11, wherein the haptic feedback includes at least one of vibratory feedback and kinesthetic feedback.

18. The method of claim 11, further comprising the steps of:

monitoring displacement of a cutting element on the distal portion of the surgical tool during the tissue stapling surgical procedure;

processing the displacement information; and communicating haptic feedback to the handle of the surgical tool, wherein the haptic feedback relates to the displacement information and informs a user of the position of the cutting element.

19. The method of claim 18, wherein the haptic feedback informs the user upon completion of the stapling procedure.

20. The method of claim 11, further comprising the steps of:

monitoring a displacement sensor located at the two opposing jaw members;

calculating the amount of tissue located within the two opposing jaw members from displacement measurements received from the displacement sensor;

preventing the firing trigger from being activated if the amount of tissue within the two opposing jaw members is inappropriate.

* * * * *